United States Patent [19]

VandenBerg

[11] Patent Number: Plant 6,334

[45] Date of Patent: Oct. 11, 1988

[54] CHRYSANTHEMUM PLANT NAMED SALMON CHARM

[75] Inventor: Cornelis P. VandenBerg, Salinas, Calif.

[73] Assignee: Yoder Brothers, Inc., Barberton, Ohio

[21] Appl. No.: 932,148

[22] Filed: Nov. 18, 1986

[51] Int. Cl.[4] ..... A01H 5/00

[52] U.S. Cl. ..... Plt./80

[58] Field of Search ..... Plt./74, 80

*Primary Examiner*—James R. Feyrer

*Attorney, Agent, or Firm*—Schwartz, Jeffery, Schwaab, Mack, Blumenthal & Evans

[57] ABSTRACT

A chrysanthemum plant named Salmon Charm particularly characterized by its flat capitulum form; decorative capitulum type; salmon ray floret color; diameter across face of capitulum of up to 11 cm at maturity when grown as a pinched disbudded pot mum; uniform eight week photoperiodic flowering response to short days; medium plant height when grown as a pinched pot mum, and by its spreading branching pattern.

3 Drawing Sheets

The present invention comprises a new and distinct cultivar of chrysanthemum, botanically known as *Chrysanthemum morifolium,* Ramat., and referred to by the cultivar name Salmon Charm.

Salmon Charm, identified as 79134G04, is a product of a mutation induction program which had the objective of creating new chrysanthemum cultivars that would expand the color range of an existing cultivar while retaining all other traits.

Salmon Charm was discovered and selected by Cornelis P. VandenBerg on May 17, 1983 in a controlled environment in Salinas, Calif. as one flowering plant within a flowering block established as rooted cuttings from stock plants which had been exposed as unrooted cuttings to an x-ray source of 2200 rads. The irradiated parent was the cultivar identified as Charm, disclosed in U.S. Plant Pat. No. 5,502.

The first act of asexual reproduction of Salmon Charm was accomplished when vegetative cuttings were taken from the initial selection in August 1983 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Salmon Charm are firmly fixed and are retained through successive generations of asexual reproduction.

Salmon Charm has not been observed under all possible environmental conditions. The phenotype may vary significantly with variations in environment such as temperature, light intensity, and day length.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Salmon Charm, which, in combination, distinguish this chrysanthemum as a new and distinct cultivar:

1. Flat capitulum form.
2. Decorative capitulum type.
3. Salmon ray floret color.

4. Diameter across face of capitulum up to 11 cm at maturity, when grown as a pinched disbudded pot mum.
5. Uniform eight week photoperiodic flowering response to short days.
6. Medium plant height, requiring 0 to 7 long days after pinch prior to short days and 1 application of 2500 ppm B-9 SP to attain a flowered plant height of 25 to 35 cm for year-round flowerings when grown as a pinched pot mum.
7. Spreading branching pattern.

The accompanying photographic drawings show typical inflorescence and leaf characteristics of Salmon Charm, with the colors being as nearly true as possible with illustration of this type. Sheet 1 is a color photograph of Salmon Charm grown as a pinched disbudded pot mum. Sheet 2 is a black and white photograph of three views of the inflorescence of Salmon Charm. Sheet 3 is a black and white photograph showing the upper and under sides of the leaves of Salmon Charm at three stages of development (mature, intermediate and immature).

Of the commercial cultivars known to the inventor, the most similar in comparison to Salmon Charm is the parent cultivar Charm. All traits of Salmon Charm are similar to those of Charm, except the color of ray florets. The color of the ray florets of Salmon Charm is salmon, as contrasted with the light lavender pink ray florets of Charm.

In the following description, color references are made to The Royal Horticultural Society Colour Chart. The color values were determined on plant material grown as a pinched disbudded pot mum in Salinas, Calif. on Mar. 24, 1986.

Classification:

*Botanical.*—*Chrysanthemum morifolium,* Ramat., cv. Salmon Charm.

*Commercial.*—Decorative disbudded pot mum.

INFLORESCENCE

A. Capitulum:

*Form.*—Flat.

*Type.*—Decorative.

*Diameter across face.*—Up to 11 cm at maturity.

B. Corolla of ray florets:

*Color (general tonality from a distance of three meters).*—Salmon.

*Color (upper surface).*—27A to 26D, overcast and streaked with179D.

*Color (under surface).*—24D, tinged with 26D.

*Shape.*—Flat, oblong.

C. Corolla of disc florets:

*Color (mature).*—154B.

*Color (immature).*—149B.

D. Reproductive organs:

*Androecium.*—Present on disc florets only, very few; scant pollen.

*Gynoecium.*—Present on both ray and disc florets.

PLANT

A. General appearance:

*Height.*—Medium; 25 to 35 cm as a pinched disbudded pot mum with 0 to 7 long days after pinch prior to short days and 1 application of 2500 ppm B-9 SP.

*Branching pattern.*—Spreading.

B. Foliage:

*Color (upper surface).*—147B.

*Color (under surface).*—148B.

*Shape.*—Lobed and serrated.

I claim:

1. A new and distinct chrysanthemum plant named Salmon Charm, as described and illustrated, and particularly characterized as to uniqueness by the combined characteristics of flat capitulum form; decorative capitulum type; salmon ray floret color; diameter across face of capitulum of up to 11 cm at maturity when grown as a pinched disbudded pot mum; uniform eight week photoperiodic flowering response to short days; medium plant height when grown as a pinched pot mum; and spreading branching pattern.

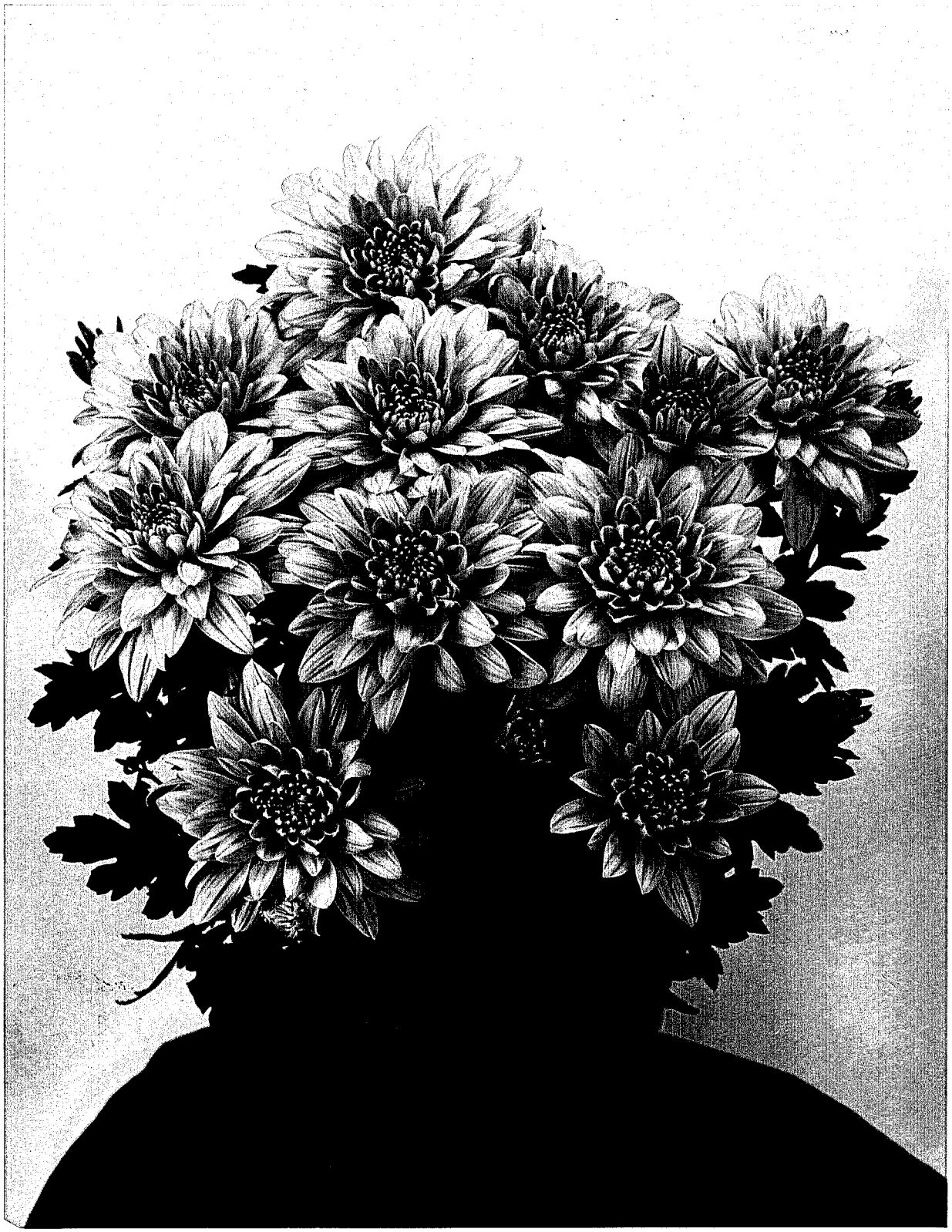

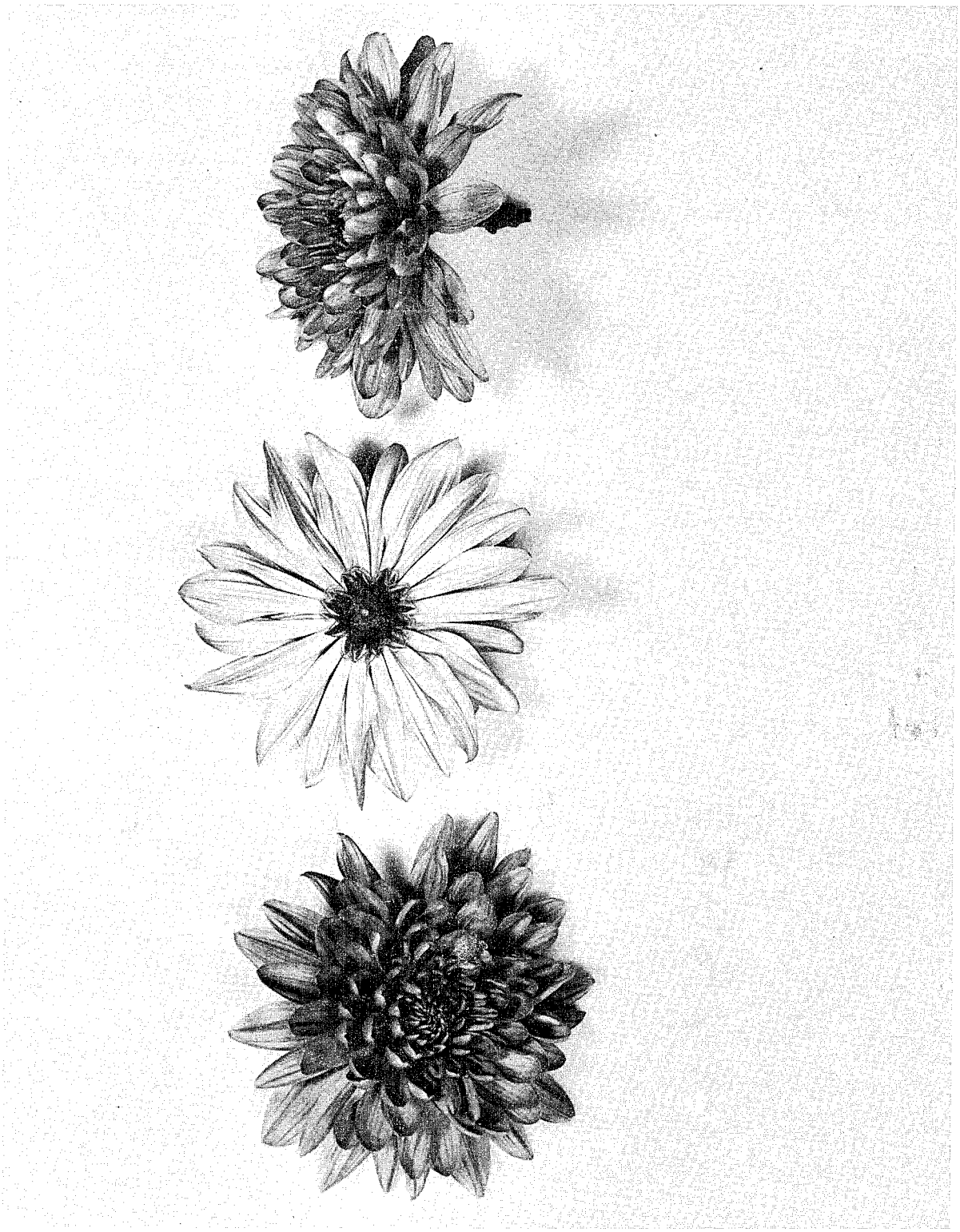

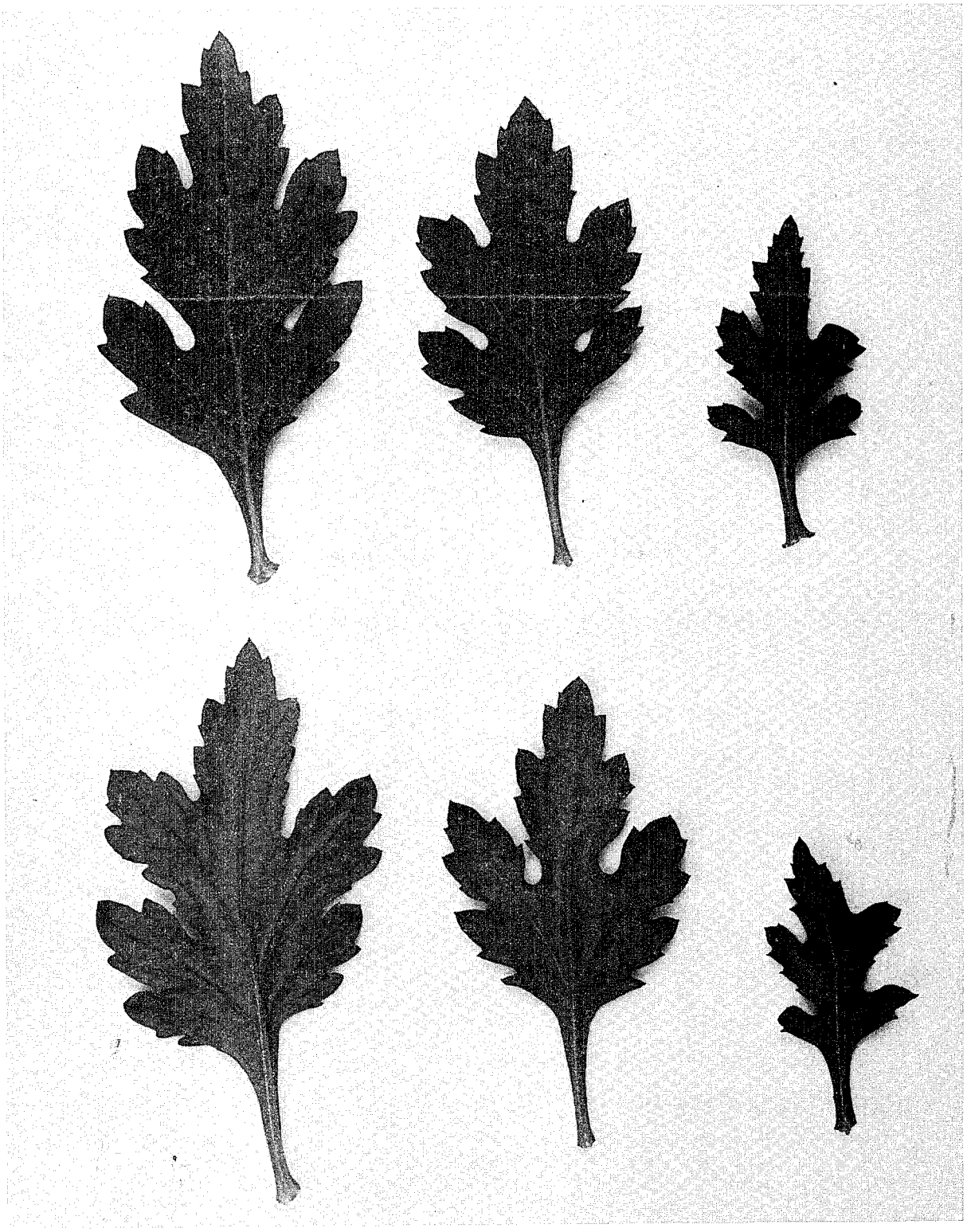

* * * * *